United States Patent [19]

Murashige et al.

[11] Patent Number: 5,596,129
[45] Date of Patent: Jan. 21, 1997

[54] PROCESS AND APPARATUS FOR PRODUCING AROMATIC CARBOXYLIC ACID

[75] Inventors: Norio Murashige; Etsuro Okamoto; Shizu Suzuki, all of Kuga-Gun, Japan

[73] Assignee: Mitsui Petrochemical Industries, Ltd., Tokyo, Japan

[21] Appl. No.: 409,085

[22] Filed: Mar. 22, 1995

[30] Foreign Application Priority Data

Mar. 22, 1994 [JP] Japan ................................ 6-050396
Apr. 1, 1994 [JP] Japan ................................ 6-065302

[51] Int. Cl.$^6$ ............................................ C07C 51/215
[52] U.S. Cl. ................................ 562/414; 562/412
[58] Field of Search ............................ 562/414, 412

[56] References Cited

U.S. PATENT DOCUMENTS

| | | | |
|---|---|---|---|
| 4,334,086 | 6/1982 | Hanotier et al. | 563/413 |
| 4,593,122 | 6/1986 | Hashizume et al. | 562/414 |
| 4,827,025 | 5/1989 | Shiraki et al. | |

FOREIGN PATENT DOCUMENTS

| | | |
|---|---|---|
| 0135341 | 3/1985 | European Pat. Off. . |
| 0261892 | 3/1988 | European Pat. Off. . |
| 2072162 | 9/1981 | United Kingdom . |

*Primary Examiner*—Gary Geist
*Assistant Examiner*—Samuel Barts
*Attorney, Agent, or Firm*—Birch, Stewart, Kolasch & Birch, LLP

[57] ABSTRACT

It is contemplated by the present invention to produce a high quality aromatic carboxylic acid by a liquid phase oxidation of an alkylbenzene by contacting it with a molecular oxygen-containing gas in a solvent containing a lower aliphatic carboxylic acid, under exclusion of any acceleration of decomposition of the solvent molecules and danger of explosion accident. The process for producing an aromatic carboxylic acid according to the present invention by a liquid phase oxidation of an alkylbenzene by contacting the alkylbenzene with a molecular oxygen-containing gas in a solvent containing a lower aliphatic carboxylic acid comprises supplying the alkylbenzene and the solvent to a reactor, supplying, as the molecular oxygen-containing gas, a high oxygen content gas containing molecular oxygen at a concentration higher than that of air to the reactor, circulating at least a part of the reactor exhaust gas as such or after having been separated from the condensable components thereof to the liquid layer in the reactor and thereby oxidizing the alkylbenzene to the aromatic carboxylic acid.

8 Claims, 2 Drawing Sheets

1

PROCESS AND APPARATUS FOR PRODUCING AROMATIC CARBOXYLIC ACID

FIELD OF THE INVENTION

The present invention relates to a process and an apparatus for producing an aromatic carboxylic acid by a liquid phase oxidation of an alkylbenzene with molecular oxygen in a solvent containing a lower aliphatic carboxylic acid, adapted especially for the production of terephthalic acid.

BACKGROUND OF THE INVENTION

Heretofore, a technique has been employed for producing aromatic carboxylic acids, such as terephthalic acid etc., in an industrial large scale, in which an alkylbenzene, such as p-xylene or the like, is subjected to a liquid phase oxidation in a solvent containing a lower aliphatic carboxylic acid, such as acetic acid, with molecular oxygen in the presence of a catalyst, such as that containing cobalt or manganese and bromine.

The aromatic carboxylic acids produced by this prior technique are contaminated with impurities of intermediates and other compounds originated from the secondary reactions, whereby the product quality of the resulting aromatic carboxylic acid, in particular, as concerns, for example, the hue of the pulverized product and the light permeability of aqueous solution obtained by dissolving it in an aqueous solution of a base, is debased considerably. For the sake of a countermeasure thereto, the reaction has hitherto been conducted by adopting severe reaction conditions by, for example, elevating the reaction temperature and increasing the catalyst concentration, under an intimate control of the reaction so as to lower the content of the impurities deteriorating the product quality.

Under such severe reaction conditions, however, a part of the lower aliphatic carboxylic acid used as the solvent will be lost during the reaction by conversion into carbon dioxide, carbon monoxide and other by-products. In general, the severer the reaction consitions, the higher will be the proportion of decomposition of the lower aliphatic carboxylic acid. Therefore, by selecting more severe reaction conditions so as to achieve a more higher quality of the product, the decomposition of the lower aliphatic carboxylic acid used as the solvent becomes greater, resulting in an increase in the running cost.

If, in contrast thereto, an oxygen-rich gas, such as pure oxygen, is employed for the molecular oxygen-containing gas, a high quality aromatic carboxylic acid can be obtained, since the occurrence of impurities badly affecting the product quality will be reduced. Here, however, the oxygen content in the gas phase in the reactor should be high enough in order to maintain a high oxygen partial pressure therein, whereby a danger of explosion of the existing easily combustible substances, such as the lower aliphatic carboxylic acid, the alkylbenzene etc., will become higher and it becomes unavoidable to limit the reactor operation condition.

In the production of an aromatic carboxylic acid by the conventional process, carbon dioxide, carbon monoxide and other by-products are discharged in accompaniment with the reactor exhaust gas. These by-products include noxious substances, such as carbon monoxide and methyl bromide, which must either be treated by any kind of purification equipment, so long as a reasonable tolerance to the environment shall be taken into account, or discharged out to the atmospheric air by an appropriate practical way in respect of the landing pollutant concentration.

The existing installations for producing an aromatic carboxylic acid, such as terephthalic acid, are usually of large scale, so that the amount of the reactor exhaust gas is also large when air is used as the molecular oxygen-containing gas. Therefore, the installations for treating the noxious substances contained in the reactor exhaust gas and for recovering by-products into useful products has to be designed also in an uneconomically vary large scale.

While the amount of the reactor exhaust gas can considerably be reduced by using pure oxygen as the molecular oxygen-containing gas, the reactor operation condition is here restricted due to the increase in the danger of explosion, as mentioned above.

Processes have hitherto been proposed for producing an aromatic carboxylic acid under recirculation of the reactor exhaust gas to the reactor (See, for example, Japanese Patent Application Kokai Nos. 36439/1985 and 83046/1988, which correspond to the U.S. Pat. Nos. 4,593,122 and 4,827,025, respectively). In the proccess of the Japanese Patent Application Kokai No. 36439/1985, however, it is difficult to attain an effect of reduction of the occurrence of impurities deteriorating the product quality by employing a high oxygen content gas having a oxygen concentration higher than that of air, since this process employs air as the molecular oxygen-containing gas to be supplied to the reactor. By the process of the Japanese Patent Application Kokai No. 83046/1988, no reduction of danger of explosion accident can be expected, when a high oxygen content gas is employed as the molecular oxygen-containing gas, since the reactor exhaust gas is returned to the gas space of the reactor.

SUMMARY OF THE INVENTION

An object of the present invention is to obviate the problems of the prior techniques for producing an aromatic carboxylic acid as mentioned above and to provide a process and an apparatus for producing an aromatic carboxylic acid permitting to produce a high quality aromatic carboxylic acid in a safe manner without causing increased decomposition of the reaction solvent.

Another object of the present invention is to provide a process and an apparatus for producing an aromatic carboxylic acid, in which a considerable reduction of the amount of the reactor exhaust gas and avoidance of the danger of explosion accident can be attained in a safe and simple manner.

The process for producing an aromatic carboxylic acid according to the present invention by a liquid phase oxidation of an alkylbenzene with a molecular oxygen-containing gas in a solvent containing a lower aliphatic carboxylic acid comprises supplying the alkylbenzene and the solvent to a reactor, supplying, as the molecular oxygen-containing gas, a high oxygen content gas containing molecular oxygen at a concentration higher than that of air to the reactor, circulating a part of the reactor exhaust gas to the liquid layer in the reactor and thereby oxidizing the alkylbenzene to the aromatic carboxylic acid.

In this process, a high oxygen content gas having a concentration of molecular oxygen higher than that of air is supplied to the reactor as the molecular oxygen-containing gas and the reactor exhaust gas is circulated to the liquid layer of the reactor. It is possible, in realizing the circulation of the reactor exhaust gas, either to return a part of the reactor exahaust gas after having been separated from the condensable components thereof or to return a mixture of the reactor exhaust gas and the high oxygen content gas to the liquid layer in the reactor.

The first apparatus for producing an aromatic carboxylic acid according to the present invention comprises a reactor for effecting a liquid phase oxidation of an alkylbenzene by contacting it with a molecular oxygen-containing gas in a solvent containing a lower aliphatic carboxylic acid, a supply line for supplying the alkylbenzene and the solvent to the reactor, a condenser for separating the condensable components of the reactor exhaust gas, a gas circulation line for circulating the reactor exhaust gas after having been subjected to separation of the condensable components thereof to the liquid phase part of the reactor and a feed line for supplying the molecular oxygen-containing gas to the reactor.

The second apparatus for producing an aromatic carboxylic acid according to the present invention comprises a reactor for effecting a liquid phase oxidation of an alkylbenzene by contacting it with a molecular oxygen-containing gas in a solvent containing a lower aliphatic carboxylic acid, a supply line for supplying the alkylbenzene and the solvent to the reactor, a gas circulation line for circulating the reactor exhaust gas to the liquid phase part of the reactor and a gas mixing unit for mixing a high oxygen content gas containing molecular oxygen at a concentration higher than that of air, supplied as the molecular oxygen-containing gas to the gas circulation line, with the reactor exhaust gas.

DETAILED DESCRIPTION OF THE INVENTION

Figure 1:
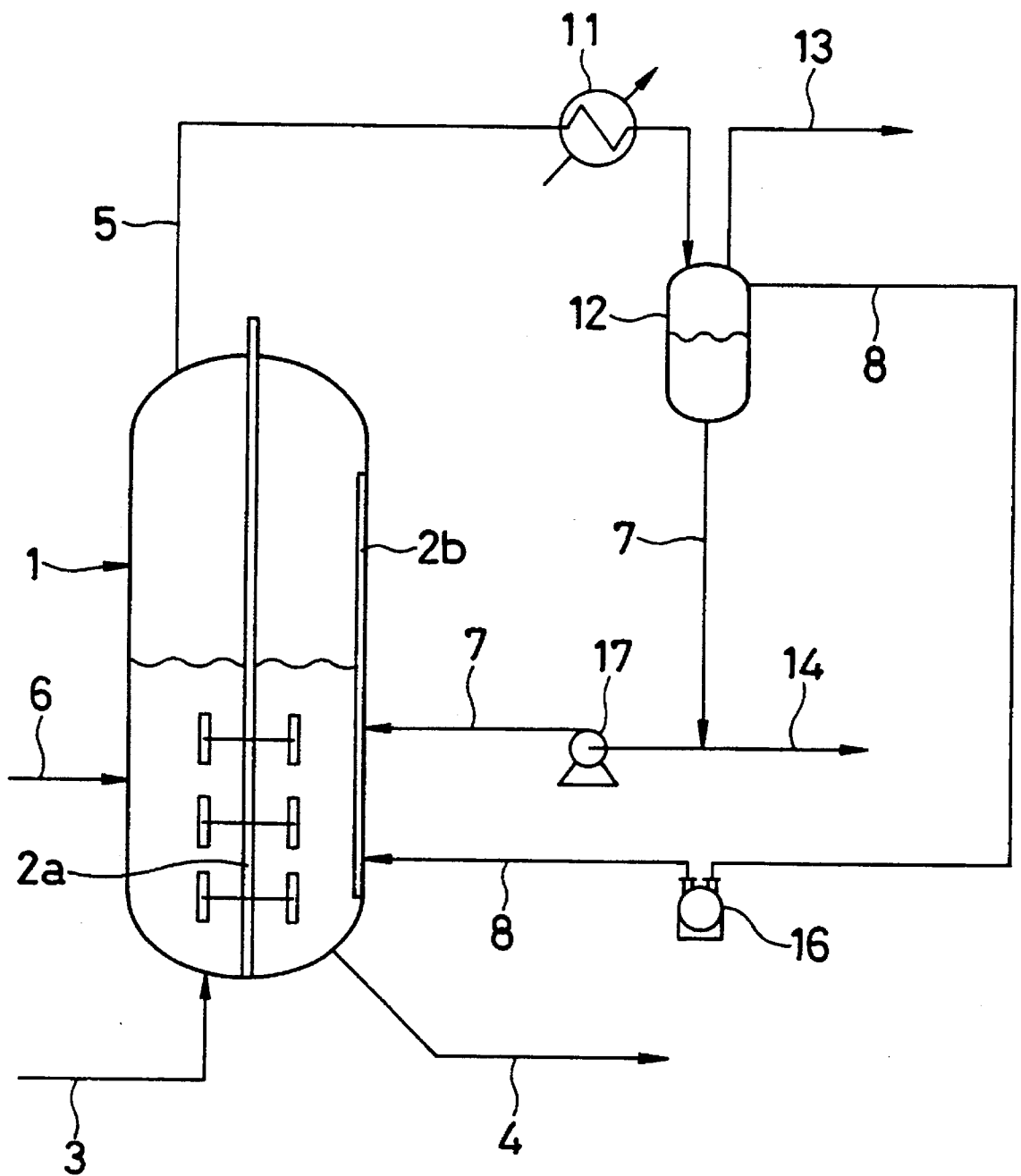
FIG. 1 is a flow diagram of one embodiment of the apparatus for producing an aromatic carboxylic acid according to the present invention, in which a high oxygen content gas and the circulating reactor exhaust gas are separately introduced into the reactor.

According to the present invention, the alkylbenzene to be used as the raw material to be converted into an aromatic carboxylic acid, such as, an aromatic mono-, di- or tricarboxylic acid may be selected among mono-, di- and trialkylbenzenes and those in which a part of the alkyl groups is oxidized. The process according to the present invention may preferably be applied to the production of terephthalic acid, in which the starting alkylbenzene may be, for example, p-xylene, p-toluic acid or a mixture of them.

The solvent to be employed for the liquid phase oxidation in the process according to the present invention contains a lower aliphatic carboxylic acid having 6 or less carbon atoms. Such a lower aliphatic carboxylic acid may be selected among, for example, acetic acid, propionic acid, butyric acid, isobutyric acid, n-valeric acid, trimethyl-acetic acid, caprioic acid and mixtures of one of these carboxylic acids with water. Among them, acetic acid or a mixture of acetic acid with water is preferred. When a water-containing solvent is used, the water content in the solvent may preferably be not higher than 20% by weight. Such a solvent may preferably be employed in such an amount that the alkylbenzene concentration in the solvent will be 1–50%, based on the weight of the solvent.

It is preferable to use an oxidizing catalyst in the oxidation reaction according to the present invention. As the oxidizing catalyst, there may be used preferably, for example, a catalyst containing a transition metal and bromine, especially a soluble catalyst containing cobalt, manganese and bromine, though the use of other oxidizing catalyst may not be excluded. The compound of cobalt or manganese to be used in such a catalyst may be bromide, a carboxylate, such as benzoate, naphthenate or acetate, or an acetylacetonate. The compound of bromine includes bromide of a transition metal, such as cobalt or manganese, hydrobromic acid, dibromoethylene and tetrabromoethyane. The catalyst may be employed in an amount of 10–5000 ppm of cobalt or 10–5000 ppm of manganese and 10–10000 ppm of bromine, based on the weight of the solvent containing the aliphatic carboxylic acid.

In the process according to the present invention, the aromatic carboxylic acid is produced by supplying the starting alkylbenzene and the solvent to the reactor and effecting a liquid phase oxydation thereof by contacting it with a molecular oxygen-containing gas within the solvent. Here, a high oxygen content gas having a molecular oxygen concentration higher than that of air is supplied to the reactor from outside the system and at least a part of the reactor exhaust gas is circulated to the liquid layer in the reactor. The high oxygen content gas and the reactor exhaust gas may be introduced into the reactor either separately with each other or after they have been mixed. In the case of the former, the high oxygen content gas is supplied to the reactor from a gas feed line and the reactor exhaust gas is returned to the liquid layer in the reactor via a gas circulation line. In the case of the latter, the high oxygen content gas is mixed with the reactor exhaust gas in a gas mixing means and the resulting mixture is supplied to the reactor. As the high oxygen content gas, pure oxygen, oxygen-enriched air, a mixture of pure oxygen with an inert gas or the like may be enumerated. The oxygen concentration in the high oxygen content gas is higher than that of air and preferably be 23–100% by volume, in particular 50–100% by volume.

Now, the explanation is first directed to the first aspect of the inventive process of the aromatic carboxylic acid production in which the supply of the high oxygen content gas and the circulation of the reactor exhaust gas are effected separately with each other.

There is no special limitation in the manner of contact of the starting alkylbenzene with the high oxygen content gas and it is possible to blow the high oxygen content gas directly into the liquid mixture of the alkylbenzene and the solvent. The high oxygen content gas is supplied in such an excess amount that the stoichiometry for the oxidation of the alkylbenzene by molecular oxygen is exceeded. In the case of, for example, producing terephthalic acid by oxidation of p-xylene, the high oxygen content gas may preferably be supplied so as to reach an oxygen feed rate of 0.1–3 N m³ (converted in the state of 0° C., 1 arm.) per 1 kg of p-xylene.

The reaction temperature may usually be settled at 160°–260° C., preferably at 170°–220° C. The reaction pressure is selected at a value at which the reaction mixture can be maintained in liquid state at the reaction temperature and may usually be in the range of 4–50 Kg/cm² gauge. The reaction duration may preferably be chosen usually in a residence time of 10–200 minutes, though it depends on the scale of the apparatus etc.

In the above-mentioned first aspect of the process, the reactor exhaust gas (vapor) discharged from the reactor is cooled to condense the condensable components thereof, such as water steam, the lower aliphatic carboxylic acid and the like, and is separated in a separator into the dry exhaust gas and the condensate. The condensate is circulated to the reactor, wherein a part of it is discharged out of the system to adjust the water content in the reaction mixture in the reactor. On the other hand, a part of the dry exhaust gas after having been separated from the condensable components is returned directly to the liquid layer in the reactor as a circulation gas. While the amount of the circulation gas may depend on the amount of the high oxygen content gas supplied to the reactor, concentration of oxygen therein and so on, it may be 0.01–500 times, preferably 0.03–200 times the volume of the gas discharged out of the system. The condensate may be returned partly or entirely to the gas space in the reactor, instead of returning to the liquid layer of the reactor.

By circulating the reactor exhaust gas in such an amount, the oxygen concentration in the gas space of the apparatus and in the exhaust gas to be discharged out of the system can be reduced to a value comparable to that in which air is employed as the molecular oxygen-containing gas, so that the danger of explosion accident may be avoided. If a high oxygen content gas having an oxygen concentration higher than that of air is supplied to the reactor and the reactor exhaust gas is not circulated to the reactor, the concentration of oxygen in the gas space of the reactor, in the reactor exhaust gas and in the dry exhaust gas resulting after the removal of the condensable components by cooling may, depending on the controlled value of the oxygen partial pressure in the reactor gas space, be increased, whereby the danger of explosion of the combustible volatile substances, such as the lower aliphatic carboxylic acid used as the solvent and the starting alkylbenzene, by the oxygen may accidentally increase. By circulating a part of the reactor exhaust gas to the liquid layer in the reactor, however, the danger of explosion accident can be evaded, since the partial pressure of oxygen in the reactor exhaust gas is reduced by the consumption of the remaining oxygen in the reactor exhaust gas during the subsequent passages through the reactor.

The circulation gas may preferably be returned to the liquid layer in the reactor at a portion not deeper than the ¾ depth of the stationary liquid layer from the stationary liquid level, in particular, from ¾ to the stationary liquid level. The "stationary liquid layer" and the "stationary liquid level" used herein mean the liquid layer and the liquid level assumed by the liquid reaction mixture in the state in which the high oxygen content gas and the circulation gas are not blown thereinto and no agitation of the reaction mixture is incorporated, respectively. By the way, the liquid level during the reaction lies somewhat above the stationary liquid level due to the "gas hold-up". The liquid level lifting effect depends mainly on the amount of gases blown into the reactor. By returning the circulation gas to the above-mentioned preferable portion of the reactor, the balance between the effect of attaining production of a high quality terephthalic acid and the effect of avoidance of the explosion hazard is improved, whereby a terephthalic acid product of more higher quality can be produced in a more safe manner.

Due to the direct supply of the high oxygen content gas having an oxygen concentration higher than that of air to the reactor, the oxygen concentration in the gas bubble of the supply gas in the reactor is higher in the above-mentioned process than that in the case where atmospheric air is used as the supply gas, so that the mass transfer rate of molecular oxygen from the gas in the bubble to the liquid phase (the reaction liqour) is higher in this process than that in the case of using air. Thus, the amount of the impurities which have harmful influences on the quality of the aromatic carboxylic acid and are formed in an oxygen lean condition is decreased, so that an aromatic carboxylic acid of higher quality, especially, in the hue of the powdery product, in the light transmittance of the aqueous Solution obtained by dissolveing it in an aqueous alkali solution can be produced.

It is possible here to obtain such a high quality product without relying on any severe reaction condition by, for example, choosing a high reaction temperature and high catalyst concentration, which may cause conversion of the lower aliphatic carboxylic acid into carbon dioxide, carbon monoxide and other by-products. Thus, the proportion of the lost lower aliphatic carboxylic acid can be rendered comparable to that in the case of using air as the molecular oxygen-containing gas, whereby an efficient production of a high quality aromatic cayboxylic acid can be attained. Here, the process does not suffer from any economic disadvantage in its practice, since there is no necessity of using a high reaction temperature nor requirement of higher catalyst concentration, so that the production of the aromatic cayboxylic acid can be attained at a lower cost.

Due to the easy control of the oxygen partial pressure in the gas space in the reactor by adjusting the feed rate of the high oxygen content gas and its oxygen concentration and/or the circulation rate of the circulation gas, also the product quality of the resulting aromatic carboxylic acid can be controlled easily. In addition, by the circulation of at least a part of the reactor exhaust gas to the liquid layer of the reactor, the oxygen remaining unreacted therein will anticipate to the reaction again, whereby the utilization of oxygen is effectively accomplished and, at the same time, the oxygen concentration can be reduced in the gas spaces in the reactor, the reactor exhaustion line and the circulation line.

It is important in the above first aspect to return the reactor exhaust gas directly to the liquid layer of the rector, preferably to the portion as noted previously, without mixing with the high oxygen content gas. Thus, the oxygen molecules in the gas bubbles of the high oxygen content gas blown into the reactor from the bottom thereof will migrate from the gas phase to the liquid phase of the reaction mixture as the bubbles float up therein and reacts with the alkylbenzene, while the volatile components by-produced in the liquid phase upon the oxidation, such as carbon dioxide, carbon monoxide etc., will be transferred into the gas phase in the bubbles, so that the oxygen concentration in the gas bubbles will be decreased as they float up in the liquid layer. Therefore, the effect of using the high oxygen content gas having a concentration of oxygen higher than that of air as the molecular oxygen-containing gas is at the highest at around the reactor bottom and decreases gradually towards the liquid layer top. In this manner, an aromatic carboxylic acid with high quality, in particular, with higher light transmittance and better pulverous product hue can be produced safely under exclusion of explosion hazard, by returning the circulation gas directly to the liquid layer, preferably at the portion mentioned above, without mixing with the high oxygen content gas.

The remainder of the reactor exhaust gas which is not returned to the reactor is discharged out of the system. The amount of the exhaust gas to be discharged out of the system corresponds to the total of the inert gas contained in the high oxygen content gas, unreacted oxygen and the by-products, such as carbon dioxide, carbon monoxide and others formed in the reactor.

The reaction mixture obtained in the manner as described above is taken out of the reactor and is subjected to a solid/liquid separation in a usual way by, for example, filtration, centrifugation and the like. The aromatic carboxylic acid separated here is then washed and dried, whereupon it can be further purified in a known manner if necessary.

Now, the description is directed to the second aspect of the inventive process for producing an aromatic carboxylic acid, in which the high oxygen content gas is supplied to the reactor after it has been mixed with the reactor exhaust gas.

The mixing proportion of the high oxygen content gas to the reactor exhaust gas (circulation gas) in the volume of the high oxygen content gas/volume of the reactor exhaust gas may desirably be within the range from 1/0.01 to 1/10, preferably from 1/0.02 to 1/5, so as to settle the oxygen concentration in the mixed gas at 15–30 voleme %.

By effecting the oxidation reaction using a gas mixture of such an oxygen concentration, the explosion hazard contingent to the case of using pure oxygen or a gas with high oxygen content can be avoided. So long as the condition for evading any explosion hazard can be selected, the oxygen concentration in the gas mixture may be higher than that given above.

There is no special limitaion in the manner of contact of the starting alkylbenzene with the molecular oxygen-containing gas (the gas mixture) and a practice of blowing the molecular oxygen-containing gas into the reaction liqour containing the alkylbenzene may be employed. The molecular oxygen-containing gas (the gas mixture) may be supplied to the reactor, so as to reach an excess of molecular oxygen than the stoichiometry of the oxidation reaction of the alkylbenzene. In the case of, for example, production of terephthalic acid by oxidation of p-xylene, it is preferable to supply the molecular oxygen-containing gas (the gas mixture) at a rate of 0.1–3 N m$^3$ of oxygen (converted for the condition of 0° C. , 1 atm) per 1 kg of p-xylene.

Other conditions for the temperature, pressure and duration of the oxidation reaction are the same as those for the first aspect of the inventive process of separate supply of the molecular oxygen-containing gas and the circulation gas to the reactor.

PREFERRED EMBODIMENTS OF THE INVENTION

Now, the present invention will further be described by way of preferred embodiments as shown in the appended Drawings.

Figure 2:
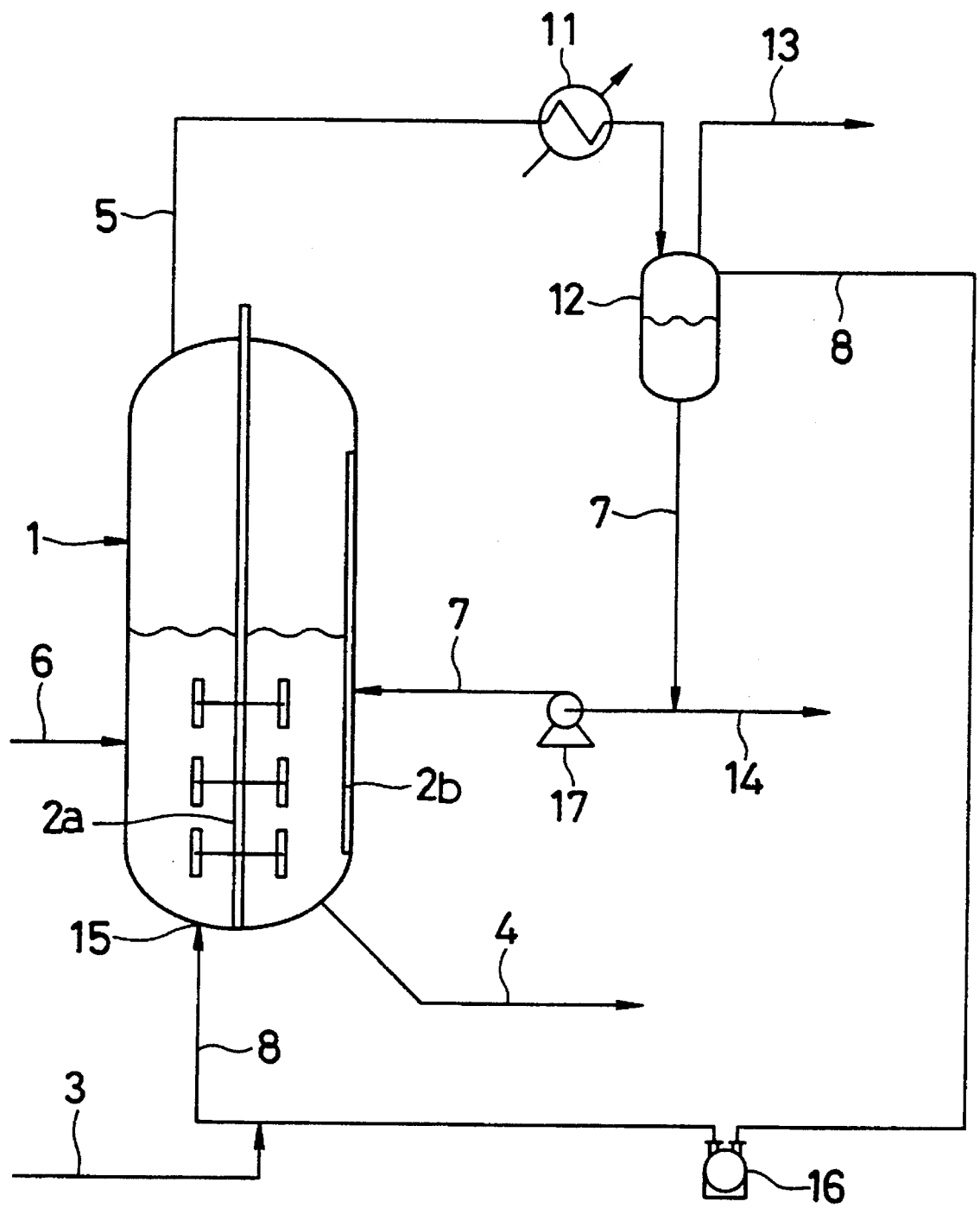
FIG. 2 is a flow diagram of another embodiment of the apparatus for producing an aromatic acrboxylic acid according to the present invention, in which a high oxygen content gas is mixed with the reactor exhaust gas before it is supplied to the reactor.

FIGS. 1 and 2 show each a flow diagram of an apparatus for producing an aromatic carboxylic acid, wherein FIG. 1 represents an embodiment of the first aspect of the inventive process supplying the high oxygen content gas and the reactor exhaust gas each isolately to the reactor and FIG. 2 represents the second aspect of the inventive process supplying them as a gas mixture. In FIG. 1, the numeral 1 indicates a reactor. The reactor 1 has a rotary vane stirrer 2a inside thereof and two vertical baffle plates 2b along the inside wall face and is connected with a feed line 3 for the high oxygen content gas at its bottom, a withdrawal line 4 for discharging out the reaction product also at its bottom, an exhaustion line 5 for the reactor exhaust gas at its top, a raw material supply line 6 for supplying the raw materials at mid portion and a condensate return line 7 also at mid portion. The reactor 1 is further connected with a gas circulation line 8 opening into the reactor at a depth from the stationary liquid level of about 2.5/4 of the stationary liquid layer full depth (namely, a portion at about 2.5/4, from above, of the liquid depth from the stationary liquid level to the bottom). The shaft of the stirrer 2a is rotatably supported at the reactor bottom and at two middle portions (not shown).

The exhaustion line 5 for the reactor exhaust gas is connected to a separator 12 via a heat exchanger 1. The condensate in the separator 12 is returned to the reactor 1 via the condensate return line 7. The reactor exhaust gas is circulated after having separated from the condensable components thereof to the liquid layer in the reactor 1 through the gas circulation line 8. The heat exchanger 11 and the separator 12 constitute a condenser. The separator 12 is connected at its top with a gas vent line 13. From the condensate return line 7, a condensate discharge line 14 branches. 16 is a compressor and 17 is a circulation pump.

In the apparatus described above, the stirrer 2a and the baffle plates 2b may be dispensed with. It is also possible to install a distillation column (not shown) in the place of, or in addition to, the heat exchanger 11.

The apparatus as shown in FIG. 2 is constructed so that the reactor 1 is connected at its bottom with the gas circulation line 8 which is connected to the high oxygen content gas feed line 3 to form a gas mixture and, thus, constitutes a gas mixing unit. Other constructions are the same as those of the apparatus of FIG. 1. In the apparatus of FIG. 2, an independent gas mixing unit, such as a gas mixing vessel (not shown), may be installed for forming the gas mixture of the circulation gas and the high oxygen content gas.

For producing an aromatic carboxylic acid by the apparatus of FIG. 1, the reactor 1 is first filled with the reaction solvent together with the catalyst, whereto a mixture of an alkylbenzene, the solvent and the catalyst is supplied via the raw material supply line 6 and the high oxygen content gas having an oxygen concentration higher than that of air is introduced directly via the feed line 3 while operating the stirrer 2a, in order to bring the alkylbenzene into contact with molecular oxygen to cause a liquid phase oxidation thereof. Due to the installation of the baffle plates 2b, a central liquid surface subsidence caused by the vortex by the rotation of the stirrer 2a is prevented and an efficient gas/liquid contact is attained.

The reactor exhaust gas is guided out via the exhaustion line 5 and passes the heat exchanger 11 to subject to cooling and condensation of the condensable components thereof, such as water steam etc., before it is separated in the separator 12 into the condensate and the dry exhaust gas. A part of the separated condensate is returned to the liquid layer in the reactor 1 via the condensate return line 7 by operating the circulation pump 17. The remainder of the condensate is discharged out via the condensate discharge line 14. A part of the dry exhaust gas having been depleted of the condensable components is returned as the circulation gas directly to the liquid layer in the reactor 1 via the gas circulation line 8 by the compressor 16.

On returning the condensate formed from the condensable components of the reactor exhaust gas to the reactor 1, a part of the condensate is extracted out of the system to adjust the circulation amount of the condensate, whereby the water content in the reaction solvent can easily be adjusted. In such a system, the adjustment of water content of the reaction solvent in the reactor is easily attainable by circulating the reactor exhaust gas after having been deprived of its condensable components in the separator 12.

The dry exhaust gas having been separated from the condensable components contains carbon dioxide, carbon monoxide and other by-products formed during the liquid phase oxidation by decomposition of the lower aliphatic carboxylic acid, in addition to the inert gases included in the high oxygen content gas supplied via the feed line 3 and unreacted remaining oxygen. Although the concentration of each component may vary depending on each specific reaction condition, the dry exhaust gas is composed mainly of the inert gases originated from the high oxygen content gas and of the by-produced carbon dioxide and carbon monoxide.

In the above aspect of the inventive process, the oxidation reaction can be effected using a high oxygen content gas supplied via the feed line 3 under the same reaction condition as in the case of supplying atmospheric air to the reactor, whereby a high quality aromatic carboxylic acid can be obtained under exclusion of explosion hazard.

If a high oxygen content gas is supplied to the reactor without incorporating the reactor exhaust gas circulation, as in the conventional process, the oxygen partial pressure is forced to be settled at a higher value, in order to maintain a reasonable oxygen partial pressure in the gas phase. If, therefore, the high oxygen content gas is passed through the reactor in a once-through principle to maintain the gas phase of the reactor under the same oxygen partial pressure as in the case of using atmospheric air, the danger of explosion by the combustible compounds, such as the lower aliphatic carboxylic acid and the alkylbenzene, will increase due to the increased oxygen concentration in the reactor exhaust gas. The reaction condition is thus limited for avoiding the explosion hazard. On the contrary, according to the present invention, no such a limitation in the reaction condition is necessary and the danger of explosion is also minimized.

The amount of the circulation gas may be 0.01–500 times or so, preferably 0.03–200 times the volume of the gas vented out of the system as mentioned above, though such amount may vary depending on the rate of supply of the high oxygen content gas via the feed line 3, the oxygen concentration thereof and so on.

The remainder of the reactor exhaust gas is vented out of the system via the gas vent line 13. The reaction product is taken out of the reactor via the product withdrawal line 4 and is subjected to a solid/liquid separation by a usual technique, such as filtration, centrifugation and so on, to separate the aromatic carboxylic acid and the solvent. The aromatic carboxylic acid obtained is processed by a known after-treatment by, for example, washing, drying and so on, followed by, if necessary, a purification by a known practice.

In the second aspect of the inventive process described above, all or a part of the condensate may be returned to the reactor gas space, instead of returning the condensate to the liquid layer in the reactor.

For producing an aromatic carboxylic acid by the apparatus of FIG. 2, the reactor 1 is first filled with the reaction solvent together with the catalyst, whereto a mixture of an alkylbenzene, the solvent and the catalyst is supplied via the raw material supply line 6 and the gas mixture is introduced via a gas mixture injection inlet 15 while operating the stirrer 2a to effect agitation, so as to bring the alkylbenzene into contact with molecular oxygen to cause a liquid phase oxidation thereof. A part of the dry exhaust gas having deprived of the condensable components is returned to the reactor 1 via the gas circulation line 8, whereto a high oxygen content gas is supplied from the feed line 3 and is mixed here with the circulation gas to form the gas mixture which is introduced into the reactor 1 via the gas mixture injection inlet 15. In the case of the apparatus of FIG. 2, the reactor exhaust gas may be returned to the liquid layer of the reactor directly via the gas circulation line 8 without removing the condensable components. Other operational procedures are the same as in the case of FIG. 1.

By preparing the gas mixture with varying mixing ratio of the circulation gas to the high oxygen content gas or the oxygen concentration in the high oxygen content gas, the oxygen concentration in the gas mixture at the injection inlet 15 can easily be controlled voluntarily. Here, the oxygen concentration of the gas mixture may preferably be adjusted at around the oxygen content of atmospheric air and may be 15–30 volume %. Selecting such an oxygen concentration, the liquid phase reaction can be conducted under the same condition as in the case of using atmospheric air, even when a high oxygen content gas having higher oxygen content is supplied via the feed line 3, whereby an explosion hazard can be evaded, so that no limitation in the reaction condition to be adopted for the case of using a high oxygen content gas with higher oxygen content should be taken into account of.

If a high oxygen content gas is supplied to the reactor without incorporating the reactor exhaust gas circulation, as in the conventional process, the oxygen partial pressure is forced to be settled at a higher value, in order to maintain a reasonable oxygen partial pressure in the gas phase, and the reaction condition should be restricted, in order to avoid the danger of explosion accident by the combustible compounds, such as the lower aliphatic carboxylic acid and the alkylbenzene. However, according to the present invention, no such a restriction in the reaction condition is necessary.

The amount of the circulation gas may be 1/0.01–1/10, preferably 1/0.02–1/5 in terms of the volume proportion of the high oxygen content gas/the reactor exhaust gas, as mentioned above, though such amount may vary depending on the rate of supply of the high oxygen content gas via the feed line 3, the oxygen concentration thereof and the oxygen concentration in the gas mixture at the injection inlet 15 etc.

There is a possibility of occurrence of an explosion hazard upon mixing the circulation gas with the high oxygen content gas supplied from the feed line 3 due to a possible increase in the content of carbon monoxide, according to the reactor exhaust gas circulation condition. In such a case, the explosion hazard can be excluded either by suppressing the occurrence of carbon monoxide through controlling the reaction condition or by incorporating a catalytic oxidation of at least a part of the circulation gas to convert carbon monoxide into carbon dioxide before mixing with the high oxygen content gas.

The remainder of the reactor exhaust gas is vented out of the system via the gas vent line 13. The amount of the vented exhaust gas corresponds to the total amount of the inert gases in the high oxygen content gas supplied via the feed line 3, the unreacted oxygen and carbon dioxide, carbon monoxide and other by-products formed in the reactor during the liquid phase oxidation. The amount of the unreacted oxygen and the by-products, such as carbon dioxide etc., can be controlled according to the reaction condition, so that the amount of the gas to be vented is determined by the amount of the inert gases included in the high oxygen content gas supplied Via the feed line 3, and thus, by the oxygen concentration of the high oxygen content gas. Therefore, the higher the concentration of oxygen in the high oxygen content gas, the smaller will be the amount of the gas vented out of the system. Here, the danger of explosion accident can be evaded, since the high oxygen content gas is served for the reaction under mixing with the circulation gas.

Below, the present invention is described by Examples of production of terephthalic acid using the apparatus of FIG. 1 or FIG. 2.

In the Examples, the concentration of carbon dioxide and carbon monoxide in the reactor exhaust gas were determined by an infrared gas analyzer. The oxygen concentration was determined by a paramagnetic oxygen analyzer. The concentration of 4-carboxybenzaldehyde (4CBA) in the terephthalic acid was determined by a liquid chromatography. The light transmittance of the terephthalic acid product is given in a per cent light transmittance of 2N aqueous potassium hydroxide solution containing 13% by weight of terephthalic acid at 340 nm. The hue (b-value) of the powdery terephthalic acid product was determined by Color Tester of SUGA Shikenki K.K. The b-value is given with appendix (+) for yellowish and (−) for bluish tint, wherein the lower its numeric value, the better is the hue.

The oxygen partial pressure in the reactor gas space is calculated from the vapor pressure of the solvent at each specific reaction pressure and reaction temperature and the concentration of oxygen in the reactor exhaust gas. As a parameter for the decomposition of acetic acid used as the solvent, the total amount of carbon dioxide and carbon monoxide (denoted hereinafter as $CO_x$ amount) in the reactor exhaust gas is employed. The higher the $CO_x$ value, the greater is the decomposition of the solvent.

EXAMPLE 1

Using the apparatus of FIG. 1, terephthalic acid was produced. As the reactor 1, a 60 liter mixing tank having two baffle plates 2b and a rotary stirrer 2a with agitation vanes in 3-stages was employed.

The reactor was charged with 19 kg of acetic acid, 1 kg of water, 50.0 g of cobalt acetate, 24.0 g of manganese acetate and 34.0 g of tetrabromoethane preliminarily and the reactor 1 was then maintained at 187° C., 11.1 Kg/cm³ gauge, whereto a feed mixture was supplied continuously at a rate of 3.3 kg/hr of p-xylene, 13.8 kg/hr of acetic acid, 0.72 kg/hr of water, 36.6 g/hr of cobalt acetate, 17.4 g/hr of manganese acetate and 24.9 g/hr of tetrabromoethane, while passing thereto via the gas feed line 3, with agitation by the stirrer, an oxygen-enriched gas having an oxygen content of 25 volume % prepared by adding oxygen to atmospheric air, in order to effect a continuous oxidation reaction.

A part of the reactor exhaust gas discharged from the separator 12 was returned to the liquid layer in the reactor 1 via the gas circulation line 8 using the compressor 16. The circulation gas was injected into the liquid layer at a depth from the stationary liquid level of about 2.5/4 of the stationary liquid layer full depth (namely, a portion at about 2.5/4, from above, of the liquid depth from the stationary liquid level to the bottom). The oxygen concentration of the reactor exhaust gas (the circulation gas) was determined to be 3 volume % and the volume rate of the circulation gas was 0.14 time the volume rate of the exhaust gas vented out of the system.

The yield of terephthalic acid, the content of 4CBA, the light transmittance value, the hue (b-value) and the by-produced amount of $CO_x$ observed are recited in Table 1. The circulation ratio for the circulation gas given in Table 1 is the volume ratio of the amount of circulation gas to the amount of the exhaust gas vented out of the system.

EXAMPLES 2 AND 3

Terephthalic acid was produced under the same conditions as in Example 1, by passing an oxygen-enriched gas having an oxygen concentration of 30 or 50 volume %, respectively, to the reactor at a reactor exhaust gas circulation ratio of 0.67 time or 2.9 times the volume rate of the exhaust gas vented out of the system, respectively. The results are recited also in Table 1.

COMPARATIVE EXAMPLE 1

Terephthalic acid was produced under the same conditions as in Example 1, except that air was used as the molecular oxygen-containing gas and criculation of the reactor exhaust gas was not incorporated. The results are recited also in Table 1.

EXAMPLE 4

Terephthalic acid was produced under the same conditions as in Example 1, except that the oxygen-enriched gas was prepared by adding oxygen to atmospheric air to reach an oxygen concentration of 30 volume % and the oxygen concentration of the reactor exhaust gas was settled at 5% by volume at a reactor exhaust gas circulation ratio of 0.74 time the volume rate of gas venting out. The results are recited also in Table 1.

COMPARATIVE EXAMPLE 2

Terephthalic acid was produced under the same conditions as in Example 4, except that air was used as the molecular oxygen-containing gas and circulation of the reactor exhaust gas was not incorporated. The results are recited also in Table 1.

EXAMPLES 5 AND 6

Terephthalic acid was produced under the same conditions as in Example 1, by passing an oxygen-enriched gas having an oxygen concentration of 25 or 50 volume %, respectively, to the reactor at a reactor exhaust gas circulation ratio of 0.92 time or 4.9 times the rate of the exhaust gas vented out of the system, respectively. The results are recited also in Table 1.

COMPARATIVE EXAMPLE 3

Terephthalic acid was produced under the same conditions as in Example 1, except that air was used as the molecular oxygen-containing gas and the reactor exhaust gas was circulated in a recirculation ratio of 0.50. The results are recited also in Table 1.

EXAMPLES 7 AND 8

Terephthalic acid was produced under the same conditions as in Example 1, by passing an oxygen-enriched gas having an oxygen concentration of 25 or 30 volume %, respectively, to the reactor at a reactor exhaust gas circulation ratio of 1.8 times or 2.7 times the rate of the exhaust gas vented out of the system, respectively. The results are recited also in Table 1.

TABLE 1

| Example or Comparative Example | Oxygen Conc. in Molecul. Oxygen-Containing Gas (volume %) | Circulation Gas $O_2$ Conc. (vol. %) | Circulation Gas Circul. Ratio | Reactor Gas Space $O_2$- Part. Pres. ($Kg/cm^2$) | Analyses of Terephthalic Acid Yield (%) | Analyses of Terephthalic Acid 4CBA Conc. (ppm) | Analyses of Terephthalic Acid Transm. (%)[1] | Analyses of Terephthalic Acid b-Value | $CO_x$ formed (mole/mole p-xylene) |
|---|---|---|---|---|---|---|---|---|---|
| Example 1 | 23 | 3 | 0.14 | 0.08 | 98 | 2400 | 65 | 2.0 | 0.31 |
| Example 2 | 30 | 3 | 0.67 | 0.08 | 98 | 2450 | 73 | 1.8 | 0.30 |
| Example 3 | 50 | 3 | 2.9 | 0.08 | 98 | 2400 | 76 | 1.7 | 0.31 |
| C. Example 1 | 21 | 3 | 0 | 0.08 | 98 | 2450 | 62 | 2.3 | 0.31 |
| Example 4 | 30 | 5 | 0.74 | 0.15 | 98 | 2350 | 76 | 1.6 | 0.32 |
| C. Example 2 | 21 | 5 | 0 | 0.15 | 98 | 2350 | 68 | 1.8 | 0.32 |
| Example 5 | 25 | 3 | 0.92 | 0.12 | 98 | 2400 | 72 | 1.8 | 0.30 |
| Example 6 | 50 | 3 | 4.9 | 0.12 | 98 | 2450 | 78 | 1.5 | 0.31 |
| C. Example 3 | 21 | 3 | 0.05 | 0.12 | 98 | 2400 | 66 | 2.0 | 0.31 |
| Example 7 | 25 | 3 | 1.8 | 0.18 | 98 | 2400 | 77 | 1.5 | 0.31 |
| Example 8 | 30 | 3 | 2.7 | 0.18 | 98 | 2400 | 79 | 1.4 | 0.31 |

Note
[1]: Light transmittance

From Table 1, it is seen that the light transmittance and the hue b-value are better for the terephthalic acid product of the inventive Examples than those in Comparative Examples of comparable conditions, showing that a high quality terephthalic acid superior in the light transmittance and hue was obtained according to the present invention. In addition, the total amount of carbon dioxide and carbon monoxide (amount of $CO_x$) in the inventive Examples is comparable to that of Comparative Examples, indicating that the decomposition of acetic acid used as the solvent is suppressed even using a higher oxygen concentration.

EXAMPLE 9

Using the apparatus of FIG. 2, terephthalic acid was produced. As the reactor 1, a 60 liter mixing tank having two baffle plates 2b and a rotary stirrer 2a with agitation vanes in 3-stages was employed.

The reactor was charged with 19 kg of acetic acid, 0.1 kg of water, 50.0 g of cobalt acetate, 24.0 g of manganese acetate and 34.0 g of tetrabromoethane preliminarily and the reactor 1 was then maintained at 187° C. and 11.1 $Kg/cm^3$ gauge, whereto a feed mixture was supplied continuously at a rate of 3.3 kg/hr of p-xylene, 13.8 kg/hr of acetic acid, 0.72 kg/hr of water, 36.6 g/hr of cobalt acetate, 17.4 g/hr of manganese acetate and 24.9 g/hr of tetrabromoethane, while passing thereto via the gas feed line 3, with agitation by the stirrer, an oxygen-enriched gas having an oxygen content of 25 volume % prepared by adding oxygen to atmospheric air so as to reach an oxygen concentration of 3.0 volume % of the reactor exhaust gas, in order to effect a continuous oxidation reaction.

A part of the reactor exhaust gas discharged from the separator 12 was returned to the reactor 1 via the gas circulation line 8 using the compressor 16 to mix it with the oxygen-enriched gas supplied from the feed line 3, so as to reach an oxygen concentration at around the gas mixture injection inlet 15 of 21 vol. % comparable to that of air.

The yield of terephthalic acid, the content of 4CBA, the light transmittance value and the amount of exhaust gas vented out of the system are recited in Table 2.

EXAMPLE 10

Terephthalic acid was produced under the same condition as in Example 9, except that the oxygen concentration of the high oxygen content gas was raised to 50 vol. % and the rate of circuration of the circulation gas was increased so as to reach an oxygen concentration at the gas mixture injection inlet 15 of 21 vol. %. The results are recited also in Table 2.

EXAMPLE 11

Terephthalic acid was produced under the same condition as in Example 9, except that the oxygen concentration of the high oxygen content gas was raised to 95 vol. % and the rate of circuration of the circulation gas was increased so as to reach an oxygen concentration at the gas mixture injection inlet 15 of 21 vol. %. The results are recited also in Table 2.

EXAMPLE 12

Terephthalic acid was produced under the same condition as in Example 10, except that the supply amount of the oxygen-enriched gas and the circulation rate for the reactor exhaust gas were changed so that the oxygen concentration of the gas mixture at the gas mixture injection inlet 15 was 23 vol. % and the oxygen concentration of the reactor exhaust gas was 3.3 volume %. The results are recited also in Table 2.

COMPARATIVE EXAMPLE 4

Terephthalic acid was produced under the same conditions as in Example 9, except that air was used as the molecular oxygen-containing gas and circulation of the reactor exhaust gas was not incorporated. The results are recited also in Table 2.

TABLE 2

| Example or Comparative Example | High O$_2$ Content Gas O$_2$ Conc. (vol. %) | High O$_2$ Content Gas Feed Rate[1] | Circulation Gas O$_2$ Conc. (vol. %) | Circulation Gas Circul. Ratio[2] | O$_2$ Conc. of the Gas Mix. (vol. %) | Analyses of Terephthalic Acid Yield (%) | Analyses of Terephthalic Acid 4CBA Conc. (ppm) | Analyses of Terephthalic Acid Transmit. (%)[3] | Vent Rate of Exhaust Gas[4] |
|---|---|---|---|---|---|---|---|---|---|
| Example 9 | 25 | 2.9 | 3.0 | 0.2 | 21 | 98 | 2450 | 62 | 2.26 |
| Example 10 | 50 | 1.3 | 3.0 | 1.6 | 21 | 98 | 2450 | 61 | 0.74 |
| Example 11 | 95 | 0.7 | 3.0 | 4.1 | 21 | 98 | 2400 | 62 | 0.09 |
| Example 12 | 50 | 1.3 | 3.3 | 1.4 | 23 | 98 | 2400 | 65 | 0.74 |
| C. Example 4 | 21 | 3.5 | 3.0 | 0 | 21 | 98 | 2450 | 62 | 2.89 |

Notes:
[1]: In N m$^3$ per kg of p-xylene
[2]: In N m$^3$ per N m$^3$ of high oxygen content gas
[3]: Light transmittance in %
[4]: In N m$^3$ per kg of p-xylene From Table 2, it is seen that the vent amount of the exhaust gas is lower for the Examples than for the Comparative Examples.

As detailed above, it is able by the process as shown in FIG. 1 according to the present invention, to produce a high quality product of an aromatic carboxylic acid, especially that excellent in the hue of powdery product and in the light transmittance of aqueous alkali solution thereof, under exclusion of the danger of explosion accident in a safe and economical manner without increasing the decomposition proportion of the reaction solvent, since a high oxygen content gas having an oxygen concentration higher than air is supplied directly to the reactor while circulating a part of the reactor exhaust gas to the liquid layer in the reactor. If the reactor exhaust gas is circulated to the liquid layer in the reactor at a depth from the stationary liquid level not deeper than the ¾ full depth of stationary liquid layer, especially to a portion from the ¾ full depth of stationary liquid layer to the stationary liquid level, the balance between the effect of attaining production of a high quality terephthalic acid product due to the supply of a high oxygen content gas of higher oxygen concentration, on the one hand, and the effect of avoidance of the explosion hazard by reducing the oxygen concentration in the gas space in the reactor, on the other hand, is improved, whereby a terephthalic acid product of more higher quality can be produced in a more safe manner.

Furthermore, it is possible by the apparatus of FIG. 1 according to the present invention, to produce an aromatic carboxylic acid of high quality under exclusion of oxidation hazard in a safe manner without increasing the rate of decomposition of the reaction solvent, since it has a condenser for removing the condensable components in the reactor exhaust gas, a gas circulation line for circulating the reactor exhaust gas which has passed the condenser to the liquid layer in the reactor and a gas feed line for supplying a high oxygen content gas having an oxygen concentration higher than that of air to the reactor.

By the process as shown in FIG. 2 according to the present invention, it is able to produce an aromatic carboxylic acid with less proportion of the reactor eahaust gas to be vented out of the system, since the amount of the inert gases introduced into the reactor is reduced as compared by the employment of air as the molecular oxygen-containing gas, by employing a gas mixture composed of the high oxygen content gas having an oxygen concentration higher than that of air and the reactor exhause gas, as the molecular oxygen-containing gas. Moreover, it is made possible by the permission of control of the concentration of oxygen in the molecular oxygen-containing gas to be supplied to the reactor by the use of the gas mixtre, to carry out the reaction under a condition similar to the case of using atmospheric air as the molecular oxygen-containing gas, if, for example, the oxygen concentration is adjusted at a value similar to that of air, whereby an explosion hazard can thus be evaded.

By the apparatus of FIG. 2 according to the present invention, it is possible to produce an aromatic carboxylic acid under exclusion of explosion hazard with less amount of the exhaust gas vented out of the system, since the apparatus is provided with a gas circulation line for circulating the reactor exhaust gas to the reactor and with a gas mixing unit for mixing a high oxygen content gas having an oxygen concentration higher than that of air supplied to the gas circulation line with the reactor exhaust gas.

We claim:

1. A process for producing an aromatic carboxylic acid by a liquid phase oxidation of an alkylbenzene with a molecular oxygen-containing gas in a solvent containing a lower aliphatic carboxylic acid, comprising supplying the alkylbenzene and the solvent to a reactor, supplying, as the molecular oxygen-containing gas, a high oxygen content gas containing molecular oxygen at a concentration of 23–100 volume % to the reactor, circulating a part of the reactor exhaust gas to the liquid layer in the reactor and thereby oxidizing the alkylbenzene to the aromatic carboxylic acid.

2. A process as claimed in claim 1, wherein the aromatic carboxylic acid is terephthalic acid.

3. A process for producing an aromatic carboxylic acid by a liquid phase oxidation of an alkylbenzene with a molecular oxygen-containing gas in a solvent containing a lower aliphatic carboxylic acid, comprising supplying the alkylbenzene and the solvent to a reactor, supplying, as the molecular oxygen-containing gas, a high oxygen content gas containing molecular oxygen at a concentration of 23–100 volume % to the reactor, circulating a part of the reactor exhaust gas, after having been subjected to removal of the condensable components, to the liquid layer in the reactor and thereby oxidizing the alkylbenzene to the aromatic carboxylic acid.

4. A process as claimed in claim 3, wherein the part of the exhaust gas is returned to the liquid layer in the reactor at a portion not deeper than the ¾ full depth of the stationary liquid layer from the stationary liquid level.

5. A process as claimed in claim 3, wherein the aromatic carboxylic acid is terephthalic acid.

6. A process for producing an aromatic carboxylic acid by a liquid phase oxidation of an alkylbenzene with a molecular oxygen-containing gas in a solvent containing a lower aliphatic carboxylic acid, comprising supplying the alkylbenzene and the solvent to a reactor, supplying, as the molecular oxygen-containing gas, a mixture of a high oxygen content gas containing molecular oxygen at a concentration of 23–100 volume % and the reactor exhaust gas to the reactor and thereby oxidizing the alkylbenzene to the aromatic carboxylic acid.

7. A process as claimed in claim 6, wherein a mixture of a high oxygen content gas and the reactor exhaust gas which has been subjected to removal of the condensable components thereof is used as the molecular oxygen-containing gas.

8. A process as claimed in claim 6, wherein the aromatic carboxylic acid is terephthalic acid.

* * * * *